United States Patent [19]

Bancalari

[11] Patent Number: 4,744,536
[45] Date of Patent: May 17, 1988

[54] COLLAPSABLE POLE AND STAND COMBINATION

[75] Inventor: Cecil G. Bancalari, Los Angeles County, Calif.

[73] Assignee: ICU Medical, Inc., Mission Viejo, Calif.

[21] Appl. No.: 843,557

[22] Filed: Jun. 25, 1986

[51] Int. Cl.$^4$ .............................................. A47G 29/00
[52] U.S. Cl. ................... 248/125; 248/166; 248/173; 248/188.6; 248/534; 248/188.7
[58] Field of Search ...................... 248/125, 129, 136.1, 248/145.6, 150, 155.3, 165, 166, 173, 188.5, 188.6, 188.7, 187, 215, 307, 322, 333, 311.3, 434, 435

[56] References Cited

U.S. PATENT DOCUMENTS

| | | | |
|---|---|---|---|
| 3,317,168 | 5/1967 | Ziph | 248/125 X |
| 3,709,556 | 1/1973 | Allard et al. | 248/125 X |
| 3,804,355 | 4/1974 | Uroshevich | 248/125 |
| 4,061,302 | 12/1977 | Boone | 248/188.6 X |
| 4,225,104 | 9/1980 | Larson | 248/125 |
| 4,278,223 | 7/1981 | Fauteux | 248/125 |
| 4,332,378 | 6/1982 | Pryor | 211/205 X |
| 4,511,157 | 4/1985 | Wilt | 248/125 X |
| 4,541,596 | 9/1985 | Price | 248/125 |

Primary Examiner—Ramon O. Ramirez
Attorney, Agent, or Firm—Whann & Connors

[57] ABSTRACT

Disclosed is a collapsable pole/stand device particularly adapted to be used to hold containers of medication for a patient so that the medication will flow under the force of gravity. The device includes a stand having inwardly collapsable legs which are mounted to a hub. Extending vertically from the central portion of the hub is a pole comprising a plurality of telescoping segments. These segments can be pulled outwardly from each other in an extended position to provide an elongated pole. Retainer members are used to secure the segments in the extended position. At the upper end of the pole is a hanger member which is secured to this end in a vertical position. At opposed end the hanger member has opened loops which enable the container to be attached to it.

11 Claims, 4 Drawing Sheets

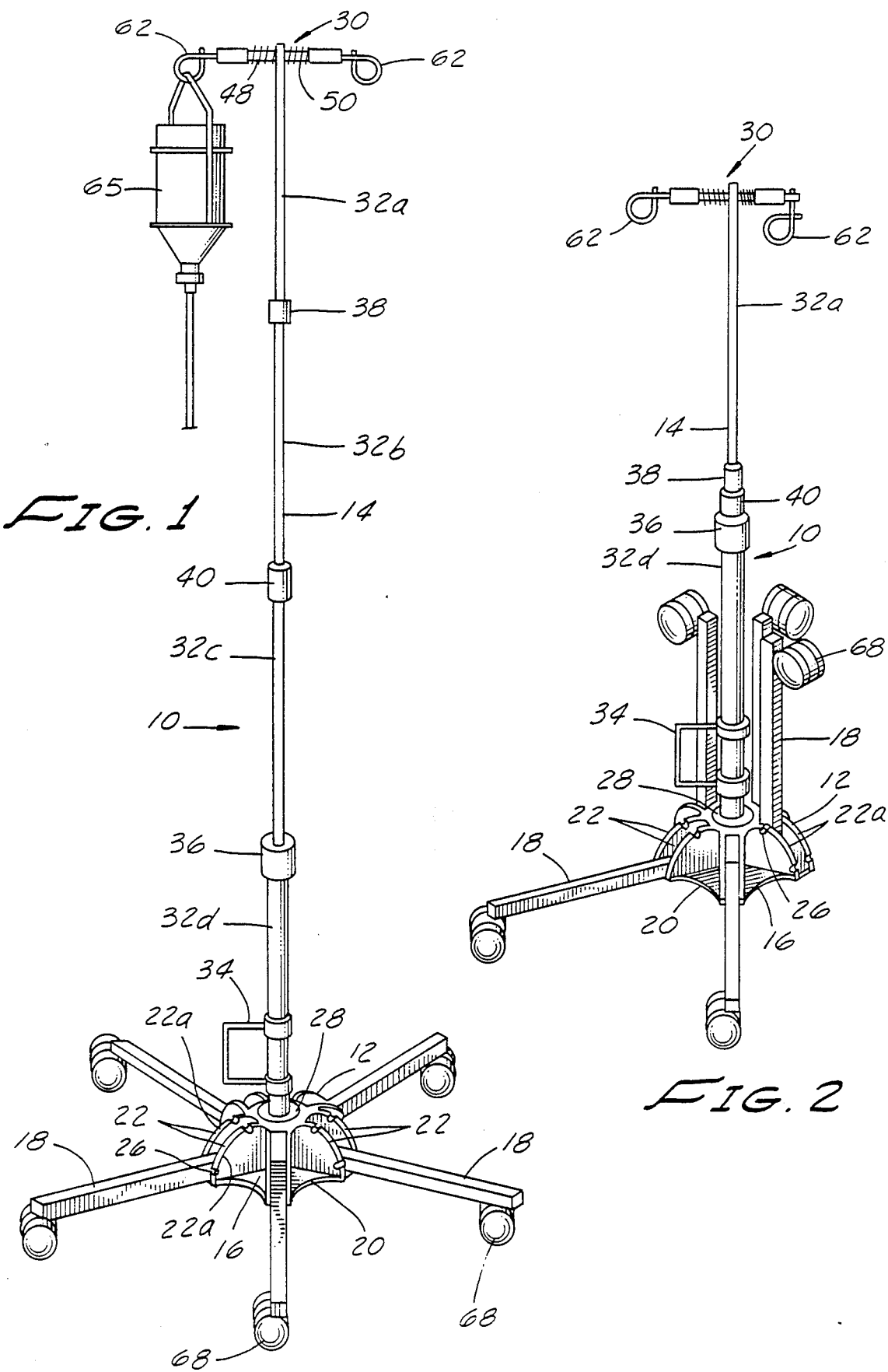

COLLAPSABLE POLE AND STAND COMBINATION

BACKGROUND OF THE INVENTION

1. Field of the Invention

This invention relates to a collapsable pole/stand device and in particular, one that is adapted to be used to administer medication intravenously in home care environments.

2. Background Discussion

With the increasing cost of hospital care, more and more patients are remaining at home. Many of these patients require that medication be administered intravenously (IV). The pole/stand combinations used in hospitals are not particularly adapted for use in homes. These pole/stand combinations are rigid structures which cannot conveniently be moved from the hospital to the home.

MAJOR FEATURES OF THE INVENTION

The present invention provides a pole/stand device which is readily collapsable and is particularly adapted for use in home environments. It is convenient to use and has several features which provide this convenience. These features of the invention all contribute to its convenience, but no signle one of which is solely responsible for its desirable attributes. Without limiting the scope of this invention, as expressed by the claims, its more prominent features will now be discussed briefly. After considering this discussion, particularly after reading the section of this application entitled Preferred Embodiment of the Invention, one will understand how the features of this invention provide the attribute of convenience.

First, the pole/stand device may be collapsable. It employs a vertically extending pole which has a plurality of telescopic segments which collapse inwardly upon one another. This pole extends outwardly from a base which carries on it legs. The base has a flat bottom which allows the structure to stand upright when the legs and pole segments have been collapsed. The legs of the pole/stand device are easily adapted to be manually manipulated. They extended outwardly in one position and pivoted inwardly into a folded position. The simple mechanical structure employed provides a strong, solid structure which prevents the pole from tipping over, yet is easily manipulated so that virtually anyone can use the pole/stand device.

Second, the pole has a hanger attached to it which includes looped ends that enable bottles of medication to be easily hung from the pole. The end sections are pivotly mounted so that they can fold inwardly. The pole/stand device of this invention thus enables the hanger to be collapsed, the pole to be collapsed, and the legs to be collapsed so that a compact structure is provided that could easily fit, for example, in the trunk of an automobile. This allows the pole device to be moved from one location to the other conveniently. A handle is also attached to the pole near the base that allows the user to easily grasp the pole device and carry it. The preferred embodiment shows the invention being used for administrating medication intravenously. This invention may also be used to administer medication in other ways also. Its main purpose is simply to provide a pole/stand device for the container of medication which will flow from its container under the influence of gravity.

BRIEF DESCRIPTION OF THE DRAWING

The drawing, where like numerals indicate like parts, depicts the preferred embodiment of this invention in which:

FIG. 1 is a perspective view of the pole/stand device of this invention in the fully extended position.

FIG. 2 is a perspective view of the pole/stand device of this invention with the pole and attached hanger partially collapsed and three of its legs folded inwardly.

DESCRIPTION OF THE PREFERRED EMBODIMENT

Figure 3:
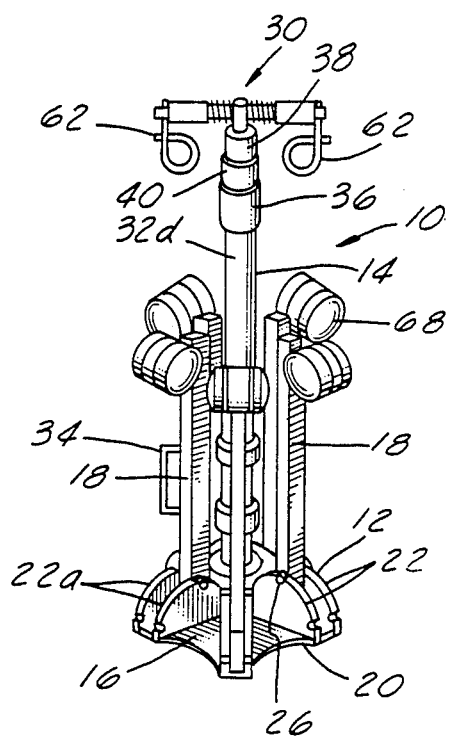
FIG. 3 is a perspective view of the pole/stand device of this invention in a fully collapsed position.

Referring to FIGS. 1 to 3, the pole/stand device 10 of this invention includes a stand 12 and a pole 14 extending upwardly in a vertical orientation from the stand. The stand 12 includes a hub and five legs extending radially outwardly from the hub. As will be discussed in greater detail below the inner end of each leg 18 connected to the hub 16 is pivotably mounted so that each leg may pivot inwardly, as illustrated in FIGS. 2 and 3.

The hub 16 has an overall hemispherical shape with a flat base 20 on which the collapsed structure may rest, as shown in FIG. 3. The hub 16 includes five pairs of plates 22 which are integral with the base 20. Each plate 22 has a curved outer edge 22a which corresponds to about one-quarter of a circle. At the opposed ends along each edge 22a are notches 24 which receive a locating finger 26 extending outwardly from each side of the rear end of the leg 18. Each leg 18 is received between the pairs of plates 22. These pairs of plates 22 are equally spaced from one another in a radial fashion. At the center of the hub 16 is a bore into which the pole is force fitted so that the lower end of the pole is secured firmly to the hub.

The pole 14 includes a hanger member 30 which is secured to the upper end of the pole and a plurality of telescopic pole segments 32a, 32b, 32c and 32d. The lower pole segment 32d is the one which fits into the bore 28 of the hub 16 and it has secured to it a handle 34. At the upper end of this segment is a nurled retainer 36 which is screwed on to threads (not shown) carried in the upper end of this segment 32d. This retainer 36 has a central opening through which fits the next adjacent pole segment 32c. When the retainer 36 is unloosened, this adjacent pole segment 32c will slide downwardly into the hollow interior of the lower pole segment 32d. The next adjacent intermediate pole segment 32b is received in the segment 32c. Each of these segments 32b and 32c have nurled retainers 38 and 40, respectively, which, when unloosened, allow the next upper segment to slide into its lower adjacent segment. Thus, as shown in FIGS. 2 and 3, by unloosening the retainer 38 and 40, the segments 32a and 32b of the poles collapsed inwardly.

Figure 4:
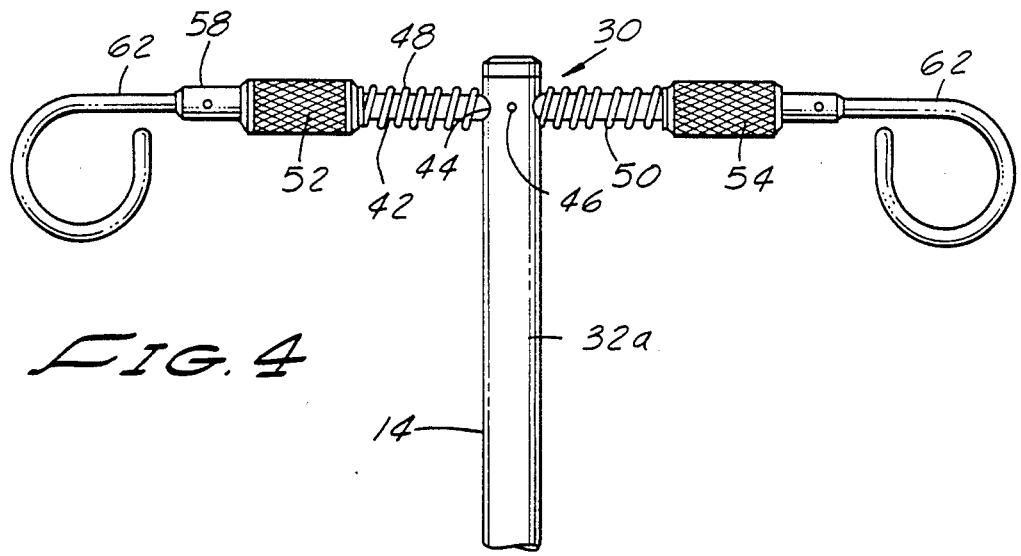
FIG. 4 is a side elevational view of the hanger member of the pole device.
Figure 5:
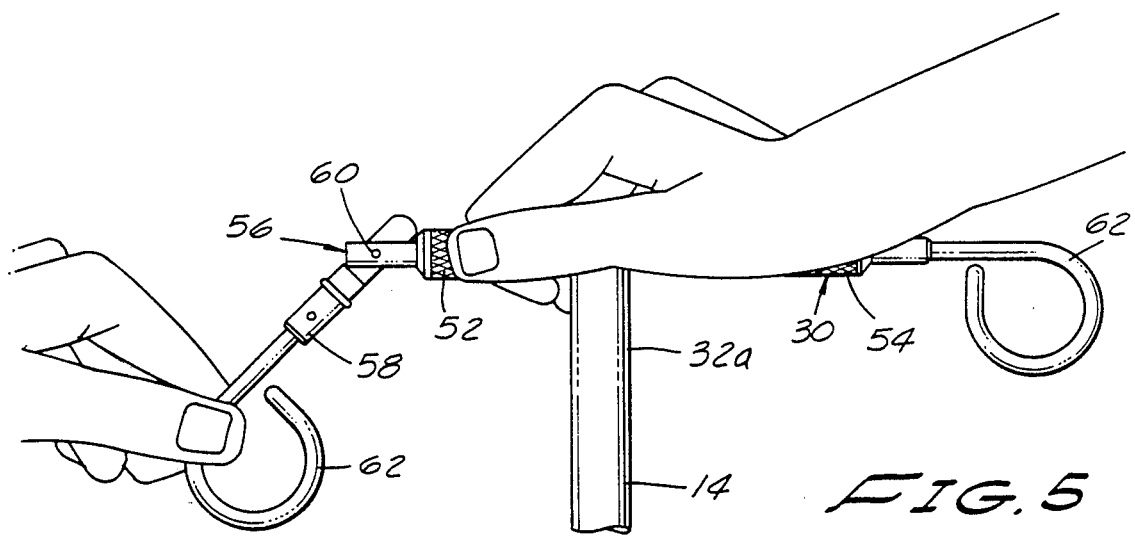
FIG. 5 is a side elevational view showing one end of the hanger member being collapsed.
Figure 6:
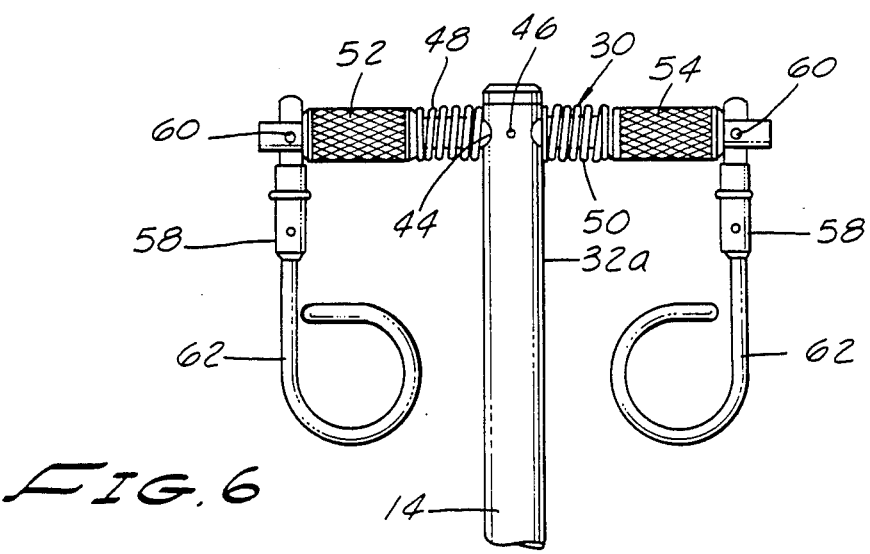
FIG. 6 is a side elevational view of the hanger member in a fully collapsed position.
Figure 7:
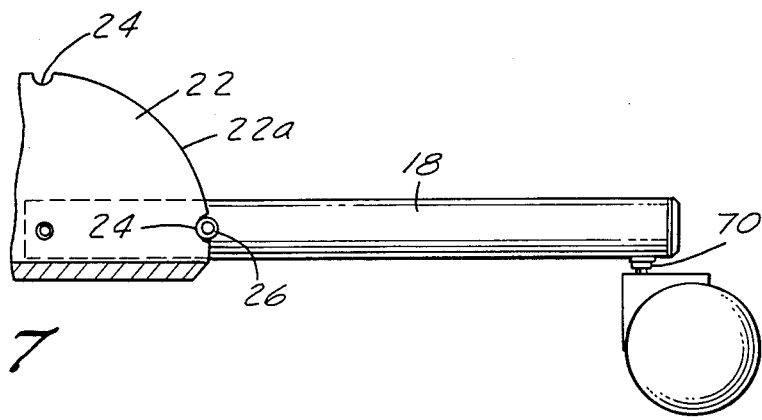
FIG. 7 is a side elevational view of one leg of the stand section of the pole device.

The hanger member 30 is best illustrated in FIGS. 4, 5 and 6. It includes an elongated tubular member 42 which fits through a hole 44 in the top pole segment 32a. At the midpoint of the tubular 42 member is a pin 46 which holds it securely in position. About this tubular member 42, wrapped around the outwardly opposed ends, are springs 48 and 50, and fitted over these ends, are two sleeves 52 and 54. When pulled back manually, as shown in FIG. 5, they expose a hinged end pieces 56, (only one shown) including a knuckle member 58, which has a pin 60 passing through it that hingley mounts the knuckle member to the end of the tubular member 42. Extending outwardly from each of the knuckle members 58 are looped ends 62. The looped ends 62 open so that the container 65 holding the medication can be attached to this looped end. This container 65 would simply have a strap or similar means that would permit the tip of the looped end 62 support the container. By manually pulling the sleeve inwardly, as shown in FIG. 5, each knuckle member 58 is exposed, allowing it to pivot and fold inwardly, as shown in FIG. 6. This compresses the springs 48 and 50, with the sleeve 52 and 54 being retained by the now vertical end of the knuckle. By pulling the sleeves 52 and 54 inwardly, one may return the looped ends 62 to their normal outwardly extending position. Upon releasing the sleeves 52 and 54, the sleeves will fit over the now horizontally disposed ends of the knuckle members 58 and retain the looped ends 62 in the horizontal position shown in FIG. 4.

Figure 10:
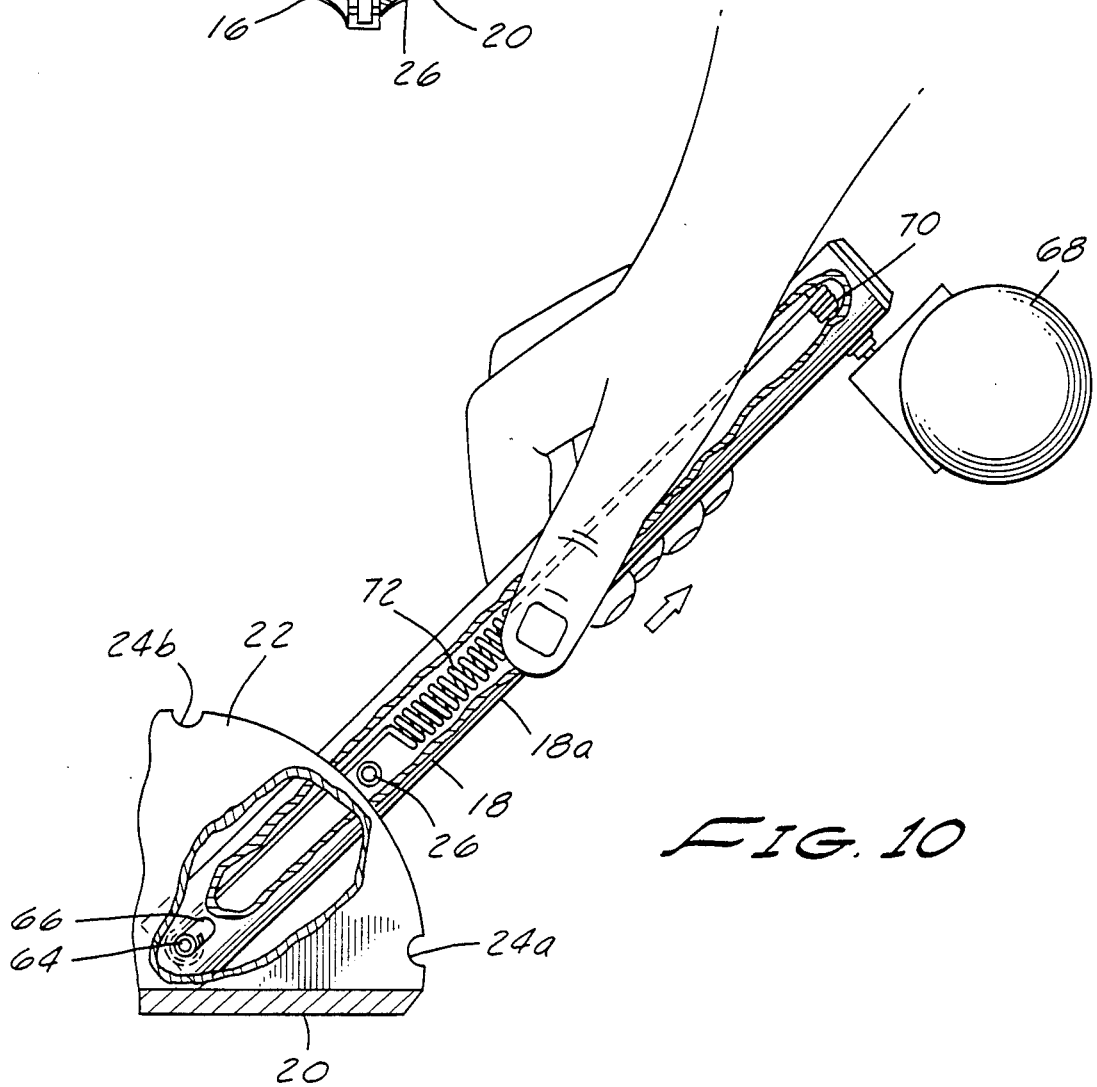
FIG. 10 is a side elevational view of FIG. 9, with sections broken away showing the internal components of the leg.

The legs 18 are best shown in FIGS. 7 through 10. Each leg includes a pin 64 which passes through the inner end of the leg and has its opposed ends receive respectively in the sides of the plates 22. As best shown in FIG. 10, the sidewalls 18a of the legs each include an elongated slots, through which the pin 64 extends. As will become apparent, this allows the leg 18 to be moved manually in and out a short distance as determined by the length of the slots.

Figure 8:
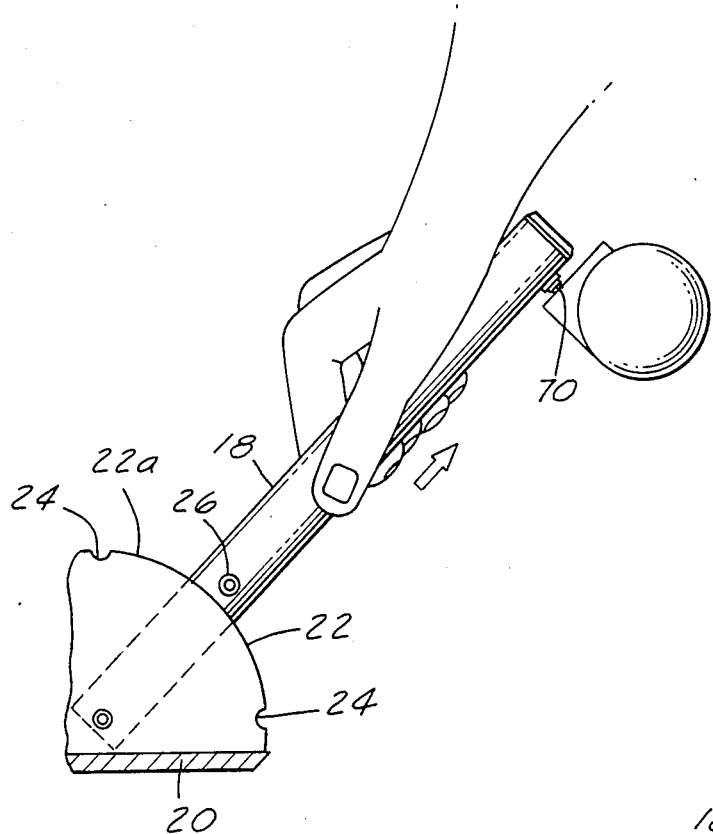
FIG. 8 is a side elevational view showing the leg of FIG. 7 being manually moved to its collapsed position.
Figure 9:
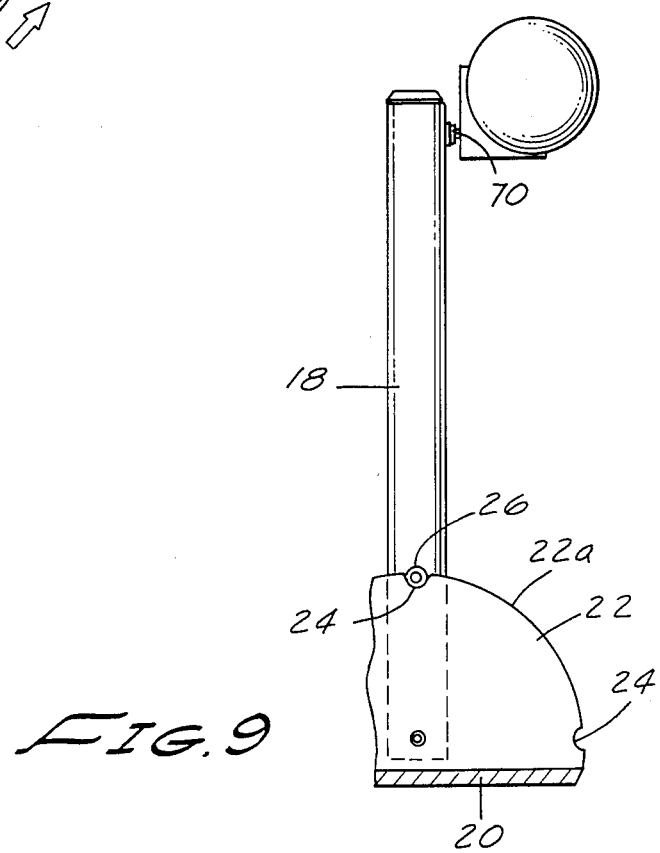
FIG. 9 is a side elevational view of the leg shown in FIG. 7 in a fully collapsed position.

Each leg 18 has a caster 68 attached to its free end. The bolt 70 holding the caster 68 extends into the leg 18 and there is a coiled spring 72 having one end secured to this bolt and its other end secured to the pin 64. This spring will normally will tend to pull the leg inwardly towards the center of the hub 16. One, however, may grasp the leg and pull it outwardly, such as shown in FIG. 8, overcoming the force of the spring. This allows the locating finger to be moved from the one notch 24a, sliding the finger along the edge 22a of the circular rim of the plates 22, until it is opposite the upper notch 24b. Upon release of the leg, the spring pulls the leg inwardly so that the retainer finger 26 is now held in the upper notch 24. Thus, the leg is held securely in the upright position when the pole is collapsed. It is also held securely in position when the leg is extended outwardly.

OPERATION

The pole/stand device 10 of this invention is very convenient to use. Its principle feature is that it is easily collapsed, yet provides a sturdy structure when opened up. Assuming the pole/stand device 10 is in the collapsed position, shown in FIG. 3 one opens it by simply grasping each leg 18 and pulling it outwardly from the sub 16 so that the locating finger is lifted from the upper notch 24b. Then the user pivots the leg 18 about the pin 64, with the retainer finger sliding along the edge 22a of the plate until the retainer finger 26 is opposite the lower notch 24a. The user then releases the leg and the spring 72 pulls the leg inwardly towards the hub 16. As mentioned above, the slot 66 limits the movement of the leg inwardly and outwardly. Each leg is thus unfolded until the five legs are displayed outwardly as shown in FIG. 1.

Next, the user unloosens each of the retainers 36, 38, and 40 for each pole segment 32b, 32c, 32d. The upper segment 32a is first withdrawn from its adjacent lower segment 32b, as shown in FIG. 2. The nurled retainer 38 is then tightened to secure this upper pole segment 32a in position relative to its lower segment 32b. Next, the segment 32b is withdrawn from the segment 32c by first loosening the retainer 40 and tightening it when the segment 32b has been withdrawn. Finally, the pole segment 32c is withdrawn from the lower most segment 32d by first untightening the retainer 36 and then tightening it. The pole 14 will now be in the position shown in FIG. 1.

The hanger member 30 is in the collapsed position shown in FIG. 6. By grasping the sleeve 52 with, for example, the right hand pointed inwardly towards the upper segment of the pole and simultaneously with the left hand, pivoting the knuckle segment 58 so that its end will be moved towards the open mouth of the sleeve as shown in FIG. 5, one pulls the looped end 62 upwardly to a horizontal position, as shown in FIG. 4. The sleeve 52 is then released. The sleeve 52 will, under the force of the spring 42, slide over the knuckle end 58 and hold the looped end 62 in the horizontal position. The pole is now in the fully extended position shown in FIG. 1 and ready to be used to hold a container 65 of medication.

SCOPE OF THE INVENTION

The above description presents the best mode contemplated of carrying out the present invention as depicted by the preferred embodiment disclosed. The combination of features illustrated by this embodiment provide the convenience and sturdiness of this of this invention. This invention is, however, susceptible to modifications and alternate constructions from the embodiment shown in the drawing and described above. Consequently, it is not the intention to limit it to the particular embodiment disclosed. On the contrary, the intention is to cover all modifications and alternate constructions falling within the scope of the invention and as genereally expressed by the following claims;

What is claimed is:

1. A collapsible pole/stand including:
   a base having a central hub and a plurality of legs extending radially outwardly from the hub, each leg having one end pivotally connected to the hub and adapted to fold inwardly and upwardly about its pivot connection to the hub,
   a vertically extending pole including a plurality of telescoping segments that allow the pole to collapse inwardly, with the smaller diameter segments being received in larger diameter segments, and means for locking the segments in the extended position and unlocking these segments to allow them to collapse inwardly, and, a hanger member secured to the end of the pole and disposed generally at a right angle with respect to the pole, said hanger member having outwardly extending end sections which are pivotally mounted to fold inwardly, and movable means that in a first position retain the end sections in an outwardly extended position and in a second position allow the end sections to be folded inwardly.

2. The device of claim 1 wherein the legs have roller elements mounted thereon to facilitate movement of the pole device.

3. The device of claim 1 wherein a handle is attached to a pole near the base.

4. The device of claim 1 wherein each leg has on its exterior a locating finger and within it a pin, a spring retainer, and a spring extending between the pin and the spring retainer, with each leg being pivoted at an end received between a pair of plates, each leg having a slot therein with the slots being aligned, with opposed ends of the pin being disposed in the plates and respectively received in each slot, and each plate including a pair of spaced notches, each notch adapted to capture the locating figure, so that with the finger in one notch, the leg is extended outwardly and adapted to stablize the pole device and in the other notch the leg is folded inwardly.

5. The device of claim 1 wherein the hanger member is an elongated tubular member with opposed open looped ends.

6. A collapsible pole/stand device including:
a base having a central hub and a plurality of legs extending radially outwardly from the hub,
each leg having on its exterior a locating finger and within it a pin, a spring retainer, and a spring extending between the pin and the spring retainer, with each leg being pivoted at an end received between a pair of plates, each leg having a slot therein with the slots being aligned, with opposed ends of the pin being disposed in the plates and respectively received in each slot, and each plate including a pair of spaced notches, each notch adapted to capture the locating finger, so that with the finger in one notch, the leg is extended outwardly and adapted to stablize the pole device and in the other notch the leg is folded inwardly.

7. The device of claim 6 wherein the hanger has outwardly extending end sections which are pivotally mounted to fold inwardly, and movable means that in a first position retains the end sections in an outwardly extended position and in a second position allow the end sections to be folded inwardly.

8. A collapsible pole/stand device including:
a base having a central hub and a plurality of legs extending radially outwardly from the hub, each leg having
(a) one end pivotally connected to the hub and adapted to fold inwardly and upwardly about is pivot connection to the hub,
(b) on its exterior a locating finger and within it a pin and a spring retainer, and a spring extending between the pin and the spring retainer,
each leg being pivoted at an end received between a pair of plates, each leg having a slot therein with the slots being aligned, with opposed ends of the pin being disposed in the plates and respectively received in each slot, and each plate including a pair of spaced notches, each notch adapted to capture the locating finger, so that with the finger in one notch, the leg is extended outwardly and adapted to stablize the pole device and in the other notch the leg is folded inwardly,
said hub having a flat bottom that enables the device with the legs folded inwardly to stand upright, resting on said flat bottom,
a vertically extending pole including a plurality of telescoping segments that allow the pole to collapse inwardly, with the smaller diameter segments being received in larger diameter segments, and means for locking segments in the extended position and unlocking these segments to allow them to collapse inwardly, and
a hanger member secured to the end of the pole and disposed generally at a right angle with respect to the pole.

9. The device of claim 8 wherein the hanger has outwardly extending end section which are pivotally mounted to fold inwardly, and movable means that in a first position retained the end sections in an outwardly extended position and in a second position allow the end sections to be folded inwardly.

10. The device of claim 9 wherein the legs have roller elements mounted thereon to facilitate movement of the pole device.

11. The device of claim 9 wherein a handle is attached to a pole near the base.

* * * * *